(12) United States Patent
Di Benedetto et al.

(10) Patent No.: US 6,692,967 B1
(45) Date of Patent: Feb. 17, 2004

(54) METHOD AND COMPOSITIONS FOR DETECTING OF BLOODSTAINS USING FLUORESCIN-FLUORESCEIN REACTION

(76) Inventors: John Di Benedetto, 398 Coronado Dr., Goleta, CA (US) 93117; Kevin Kyle, 2170 Lundhurst Ave., Carmarillo, CA (US) 93010; Terry Boan, 330 Hurst Ave., Ventura, CA (US) 93001; Charlene Marie, 398 Coronado Dr., Goleta, CA (US) 93117

( * ) Notice: Subject to any disclaimer, the term of this patent is extended or adjusted under 35 U.S.C. 154(b) by 0 days.

(21) Appl. No.: 09/894,301

(22) Filed: Jun. 27, 2001

Related U.S. Application Data
(60) Provisional application No. 60/217,360, filed on Jul. 11, 2000.

(51) Int. Cl.$^7$ ................................................. G01N 21/76
(52) U.S. Cl. .......................... 436/63; 436/66; 436/166; 436/172; 356/39; 422/61
(58) Field of Search ............................ 436/63, 66, 74, 436/166, 172; 356/39; 422/61

(56) References Cited

U.S. PATENT DOCUMENTS

| | | | | |
|---|---|---|---|---|
| 4,249,412 A | * | 2/1981 | Townsend, III | 73/40.7 |
| 5,705,470 A | * | 1/1998 | Faris | 510/403 |
| 5,976,886 A | * | 11/1999 | Cheeseman | 436/63 |

OTHER PUBLICATIONS

Roberts et al. "Basic Principles of Organic Chemistry" 2d ed., 1977, pp. 819–820.*

* cited by examiner

*Primary Examiner*—Jeffrey Snay
(74) *Attorney, Agent, or Firm*—Philip J. Anderson; Anderson & Morishita, LLC

(57) ABSTRACT

A method, compositions and kit are set forth for detecting blood stains. A reactant solution includes fluorescin solubilized (reduced) in acetic acid in ethanol. The solution may be buffered to a pH of approximately 9. After spraying the reactant solution on the suspected area an oxidizer is applied to promote the fluorescin to fluorescein reaction with the blood. The reacted fluorescein is then detected through luminescence for capture by photography.

11 Claims, 3 Drawing Sheets

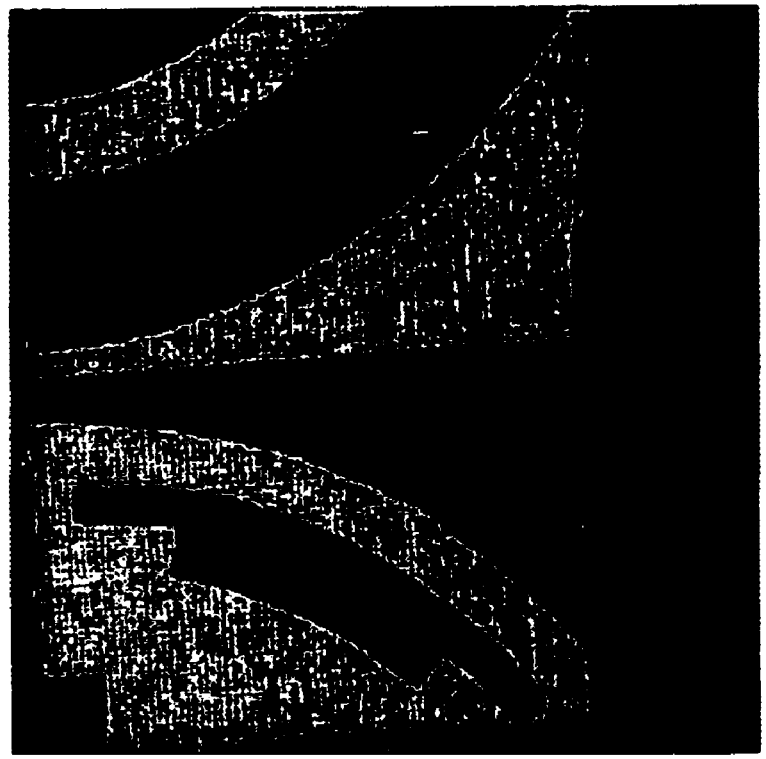
FIG. 1A Before spraying
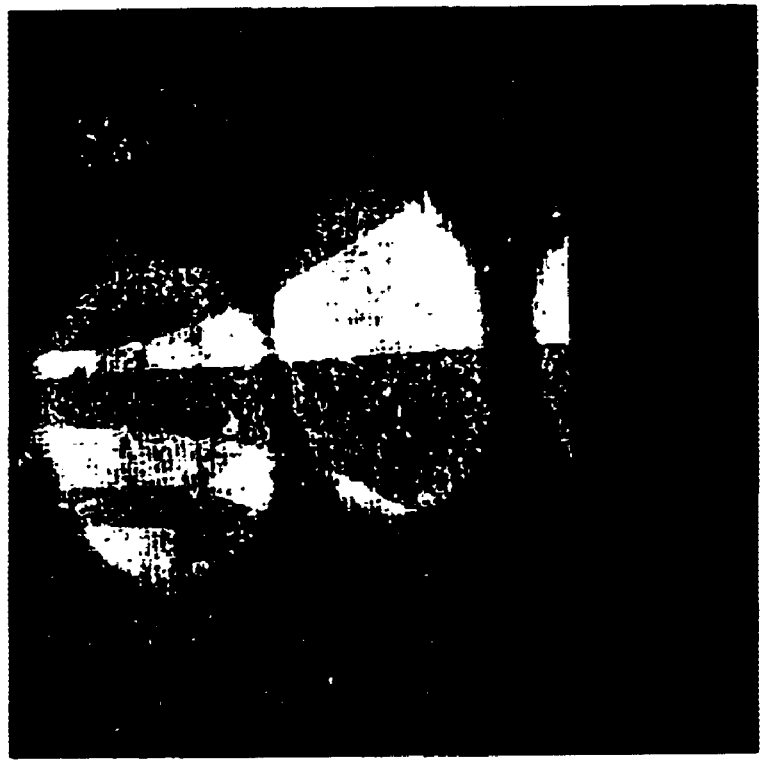
FIG. 1B After spraying with fluorescin, polymer and AMP buffer in ethanol

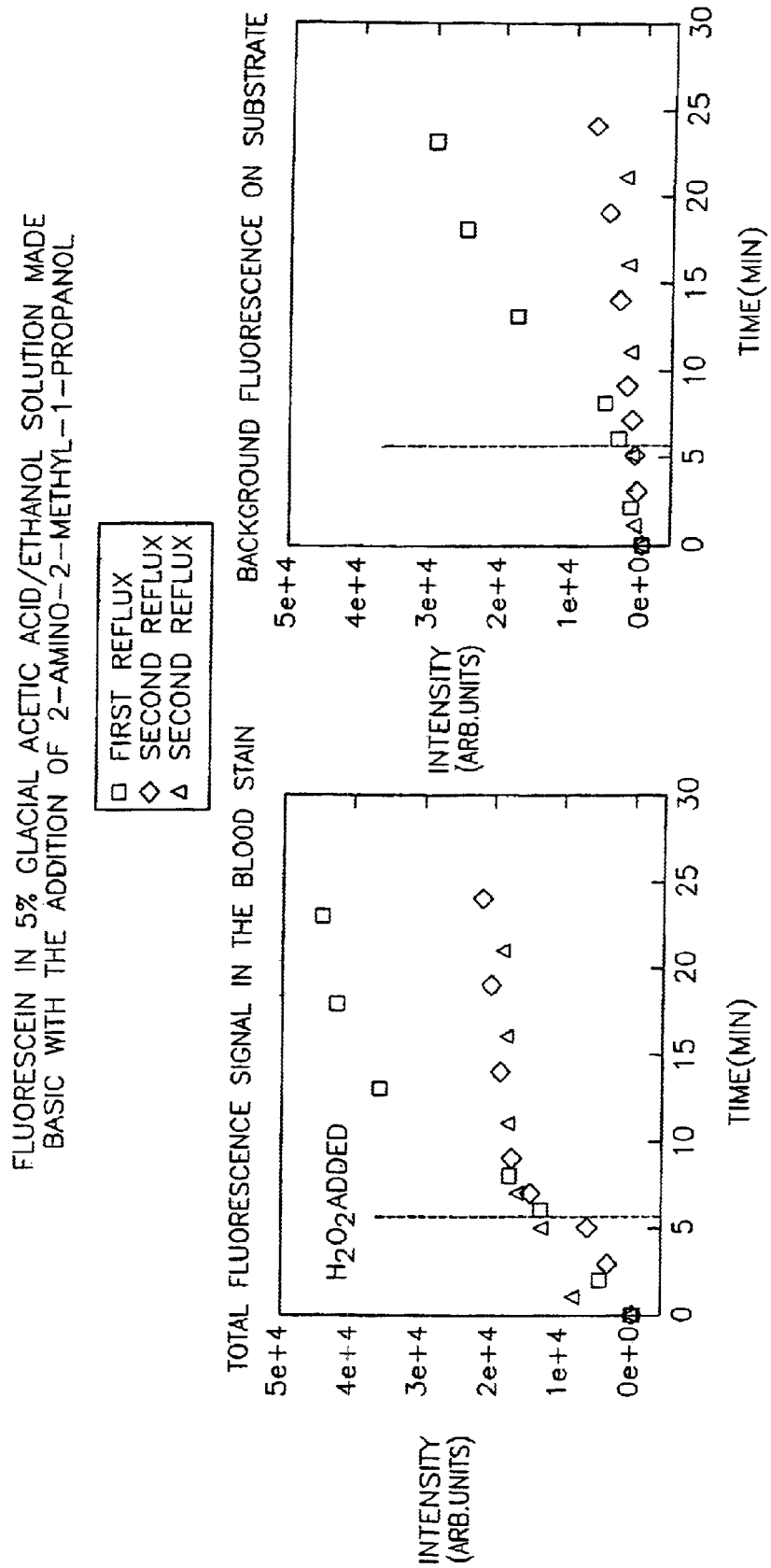

METHOD AND COMPOSITIONS FOR DETECTING OF BLOODSTAINS USING FLUORESCIN-FLUORESCEIN REACTION

CROSS-REFERENCE TO RELATED APPLICATION

The present invention claims benefit of a prior filed provisional patent application Ser. No. 60/217,360 filed Jul. 17, 2000 and titled "Fluorescein Detection Method and Solution Therefor."

GOVERNMENT LICENSE RIGHTS

The U.S. Government has a paid-up license in this invention and the right in limited circumstances to require the patent owner to license others on reasonable terms as provided for by the terms of DOE-AC08-96NV11718 awarded by the United States Department of Energy.

FIELD OF THE INVENTION

The present invention relates to luminescent methods and compositions for detecting blood using the fluorescin to fluorescein reaction.

BACKGROUND

There are various method for detecting latent, blood-based fingerprints, palm prints and footprints at, for example, a crime scene. One such technique relies on chemiluminescence of LUMINOL (5-amino-2,3-dihydro-1, 4-phthalazine) which is sprayed on the area suspected of containing blood. Oxidation of the LUMINOL in the presence of iron and peroxides found in blood is accompanied by emission of light that lasts for several seconds. A drawback of using LUMINOL is that the detection must be done in the dark to detect the emission of light, the chemiluminescence lasts for only several seconds and is not suitable such as to obtain results from a black substrate.

More recently, criminalists and crime scene investigators have used the reaction of fluorescin to fluorescein to detect the presence and pattern of bloodstains. Such a technique is as described in Cheeseman, U.S. Pat. No. 5,976,886 issued Nov. 2, 1999 the disclosure of which is hereby incorporated by reference. In this patent there is described a method for detecting latent bloodstains by applying a fluorescin solution thickened by addition of a gum compound followed by a dilute hydrogen peroxide solution to enhance the conversion of fluorescin to fluorescein and illuminating the area with UV light causing the fluorescein to fluoresce to expose the print for capture such as by photography. Te Cheeseman recipe uses water as the solvent. This stems from the original waterbased fluorescin work by Macieri and Monk. A drawback of this technique is that the fluorescin reagent according to this reference is caustic, water-soluble and has a short shelf life. The caustic nature of the solution can permanently damage the substrate being tested such as furniture, aluminum window frames and the like and may be hazardous to skin contact. The water solubility tends to result in loss of ridge detail for, for example, a fingerprint on a vertical surface such as a wall. Preserving ridge detail is crucial in matching a latent fingerprint, palm print or the like. The short shelf live requires the solution to be made relatively fresh and would undoubtedly lead to waste as aged solutions wold have to be discarded. Further there is risk that an aged solution may be used perhaps jeopardizing the collection of evidence.

Synthesis of fluorescin solutions in formic acid has been attempted, however formic acid is toxic, the reagents described are more expensive and ridge detail would probably be lost in the formic acid formulation.

There is a need for a method, solutions and kit for detection of blood stains which is non-toxic, will not damage the surface being examined, which has a longer shelf life and which provides for the fluorescin to fluorescein reaction in a less caustic solution and which is believed to result in greater detail being exhibited as well as providing for longer exhibition times for the fluorescing results. The kit preferably includes components which can be pre-formulated and wherein such formulation provides for preservation of ridge detail of the print.

SUMMARY OF THE INVENTION

Toward this end a solution and method are set forth for detecting blood stains, which preserves ridge detail, which is less caustic and less toxic, which provides for longer reaction exhibition and which substantially overcomes the drawbacks noted above.

Accordingly, the method includes applying to the area suspected of containing blood a reactant solution containing either fluorescein or dichlorofluorescein solubilized in acetic acid and ethanol with a metal reducing agent such as, for example, zinc, magnesium or aluminum. The reduction to fluorescin can be completed by one of two methods: cold solubilization or reflux solubilization. In room temperature solubilization, fluorescein or dichlorofluorescein is added to acetic acid and ethanol in a vial with a powdered metal such as zinc. The solution is lightly shaken or warmed until the yellowish color turns-clear. In the reflux solubilization, the solution should be refluxed over mossy zinc for about two hours to reduce the fluorescein, which has a yellowish color, to fluorescin which is a substantially clear solution. A buffering agent can be added to buffer the pH of the refluxed solution to a pH of between 8 and 10 and preferably to a pH of approximately 9 to increase brightness. The buffering agent is preferably an organic a mine buffer such as 2-amino-2-methyl-1-propanol in ethanol is added to the reactant solution until said solution has a neutral or slightly basic pH, e.g. a pH of approximately 9. When shelf life of the mixed solution is critical, the buffering step is ignored to increase solution stability.

Where print detail is critical on shiny surfaces that do not wet, there are two methods to decrease surface tension and the resulting spotted deposition. The surface can be pre-sprayed or dipped with/in a thin polymer solution and dried. The surface tension is lowered and the solutions will wet better producing better ridge detail. In the second method to reduce spots, a small amount of non-ionic surfactant is sprayed on the surface. These surfactants include fluoro-surfactants that can be sprayed at very low concentrations.

In one embodiment the reactant includes a Compound A of dry fluorescein with granular zinc or other metal reducing agent such as calcium, aluminum or magnesium. Since the presence of iron will poison the reduction, the reducing agent should be free of iron. Prior to application on the area suspected to have a blood stain, acetic acid and ethanol are added to solubilize compound A and mixed such that the reducing agent reduces the fluorescein to fluorescin. Reduction causes the solution to turn from a yellowish color to clear. The clear, fluorescin reactant solution is nebulized onto the suspected area.

The fluorescin of the reactant oxidizes with the blood to produce in those areas where blood is present, fluorescein.

To enhance the reaction, a Compound B oxidizing agent such as sodium metaborate, monosoduim metaborate, sodium borate or the like in a dry form or liquid sodium metaborate, monosoduim metaborate or sodium borate in alcohol or water or hydrogen peroxide. For example Compound B may include hydrogen peroxide which can be a 2–3% solution in water or a 3–5% in acetone from a 30% stock solution. Each of these oxidizing agents is used to produce an oxidizing solution, or produce hydrogen peroxide, or directly oxidize the blood on contact. Sodium metaborate has the advantage over a hydrogen peroxide solution in that sodium metaborate has a longer shelf life, is suitable for use in a kit form and provides a more controlled supply of oxidizer, or rate of peroxide formation when compared to spraying hydrogen peroxide directly.

Afer application of the fluorescin, the oxidizer is dusted or nebulized over he suspected area.

In response to UV light or blue light, e.g. wavelengths of approximately between 400 and 500 nm, the reacted fluorescein fluoresces for photographic or digital image collection of the blood print.

The compositions according to the present invention includes the synthesized and refluxed fluorescin/dichlorofluorescin reactant solution in acetic acid and ethanol which can be buffered to substantially neutral or only just basic as well as the use of the polymer and oxidant described above. The reactant solution can be provided in a kit, whereas, where the oxidizer is a hydrogen peroxide solution, should be made fresh. Where the oxidizer is a dry powder having a greater shelf life, it can be provided in a sealed container for use in the kit form. The kit would then be composed of a powdered fluorescent dye indicator, a powdered or solution of oxidizer and a bottle of ethanol.

Thus it is an object of the present invention to provide a method for detection of blood on a substrate using the fluorescin to fluorescein reaction wherein the reactant solution is not caustic, easy to mix, and preserving of ridge detail.

It is a further object to provide a reactant solution wherein the reactant is synthesized in acid and then may be buffered to the desired pH.

It is a further object to provide a reactant solution that has a greater shelf life that compositions heretofore utilized.

It is a further object to produce a composition that results in an intense and relatively persistent luminescence.

It is another of the present invention to provide a method for detection of blood an a substrate using the fluorescin to fluorescein reaction wherein the reactant solution is not caustic.

It is still a further object to provide compositions and method which are well suited to being provided in a kit form.

BRIEF DESCRIPTION OF THE DRAWINGS

These and other features and advantages will become appreciated as the same becomes better understood with reference to the description, claims and drawings wherein:

FIGS. 1A and 1B are views of a black/grey cotton fabric before and after treatment with the method and compositions of the present invention;

FIGS. 2A and 2B are graphs showing the relative intensities of luminescence of a blood stain and background on a substrate.

DESCRIPTION

Figure 3:
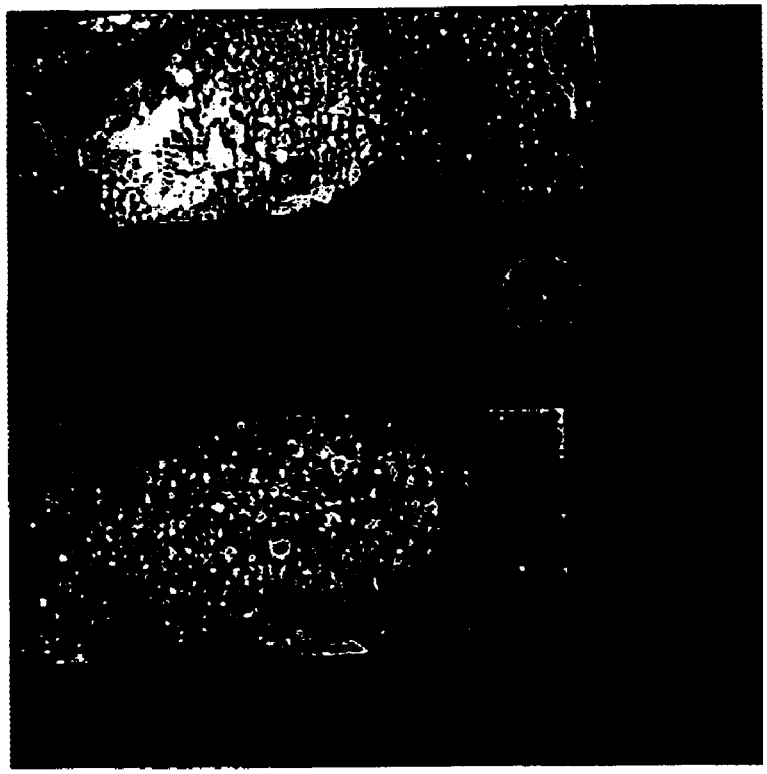
FIG. 3 shows a comparison between detail of a fluorescin solution in water (NaOH) and the solution according to the present invention on blue magazine paper.

The solutions, compositions and methods according to the present invention are particularly useful in detecting and exhibiting blood stains on a substrate which may be a fabric substrate such as fabric furniture, curtains or drapes or other substrates such as glass, plastic, wood, paper or the like. Further, it should be understood that while the present invention is described herein in reference to a substrate bearing a blood stain, that the substrate need not be any particular material and need not be flat or in any spacial orientation.

The methods and composition according to the present invention use the reaction of fluorescin to fluorescein in the presence of blood and more particularly the presence of peroxidases and heme components of blood. When so reacted, the exhibited fluorescein can be detected through luminescence.

With the foregoing in mind, the various embodiments of the methods and compositions according to the present invention will now be described.

Method/Compositions No. 1

The method and compositions according to this embodiment include preparation of a reactant Composition A solution containing fluorescin or dicholorofluorescein solubilized in alcohol. Preferably the reactant solution is prepared as follows. A 4-mM solution of fluorescein or dicholorofluorescein is solubilized in 5–10% acetic acid and ethanol solution (from glacial). This solution is combined with a reducing agent to convert fluorescein or dichlorofluorescein, having a yellowish color, to fluorescin, which is substantially a clear solution. The reducing agent can be metals such as zinc, calcium, magnesium, aluminum or other suitable reducing agent. Since the presence of iron may poison reduction, the reducing agents should be free of iron. Preferably, the reflux with the reducing agent is accomplished by slightly warming in the presence of a finely divided, reducing metal, or by refluxing for approximately 2 hours over mossy zinc. The resulting solubilized solution may be slightly pink. In the refluxed method, after cooling over zinc at room temperature a second reflux with fresh zinc is preferred. Once prepared according to the above, the reactant solution should always be stored with zinc in the container.

The foregoing solution is acidic. To buffer the solution to neutral or slightly basic having a pH of between approximately 8 and 10, the refluxed solution may be buffered with, for example, an organic amine buffer to increase brightness. Preferably the buffer includes 25 grams of 2-amino-2-methyl-1-propanol (AMP) to 5 mL of ethanol which is added to buffer the solution of the reactant composition A to a pH of approximately 9. This AMP buffer is added drop wise to the reactant solution until the desired pH.

To examine a substrate for the presence of blood and to detect and record, for example, the pattern of the detected blood, e.g. a fingerprint, the reactant fluorescin solution of Composition A is preferably applied to the suspected area by spray. The spray can be a mechanical spray as by, for example, a pump spray or can use a propellant to nebulize the solution onto the suspected area. The finer mists will produce the most ridge detail. The fluorescin solution can be stored in a spray bottle or pressurized container in a kit for future use.

While the fluorescin to fluorescein reaction is oxidized by air and blood components, preferably, a Compound B oxidizer is applied during the reaction to obtain better results. The preferred oxidizer can be a 3–5% hydrogen peroxide solution in ethanol made from a 30% stock solution. The oxidizer can also be a 2–3% water based hydrogen peroxide, however, where finger prints are suspected, this oxidizer may result in the loss of ridge detail. The oxidizer should be made fresh for application in that the peroxide does not have a long shelf life and produces oxygen in basic solutions.

Alternatively, the oxidizer can be sodium metaborate, monosoduim metaborate or sodium borate powder or sodium metaborate, monosodium metaborate or sodium borate powder in an ethanol or water solution. After application of the fluorescin solution, the dry oxidizer would be dusted onto the surface to oxidize the fluorescin to fluorescein. Where the oxidizer is a hydrogen peroxide or other liquid solution, after the reactant solution has been applied to the area suspected of containing blood, the oxidizer is applied, also preferably by a spray.

The reaction, as stated above, results in fluorescein in the pattern of the latent blood. The fluorescein is thereafter caused to luminesce by shining ultra violet light or preferably blue light (400–500 nm) on the suspected area. The luminescing fluorescein can be photographed, captured digitally or videoed to archive the results as evidence or the like.

If it is suspected that finger and/or palm prints in blood may be present, in the preferred embodiment, particularly on a vertical surface, ethanol is preferred as the solvent. If there are surfaces that are very shiny or show the formation of droplets (beading), an inert pre-spray of solution additive can be used to decrease the surface tension and wet the surface. The pre-spray or additive may be a polymer of the type used in cosmetic hair sprays such as acrylates copolymer, or a surfactant can be used to lower the surface tension without dissolving the blood. According to one embodiment of the method the additive may be included in the buffer solution by adding about 0.03 g of polymer for every 1 ml of buffer solution. The additive should be suitable for the application, i.e. be suitable in cold weather applications where applicable.

An alternative method is to first spray the additive, e.g. surface tension reducing additive, on the suspected area and permit the solution to dry before applying the fluorescin solution and oxidizer.

With reference to FIGS. 1A and B, a fabric specimen is shown before and after application of the compositions according to the method of the present invention. In FIG. 1A there is no discrete evidence of the presence of blood or prints. The area was sprayed with the buffered fluorescin reactant solution containing the polymer. After the solution dried, the hydrogen peroxide oxidizing solution was sprayed on the area to promote the oxidation of the fluorescin to fluorescein reaction. The oxidizing solution was sprayed approximately five minutes after application of the reactant solution. The Compound B oxidizing solution/powder can be applied immediately after the application of the reactant solution. In excitation light, and as shown in FIG. 1B, the prints in blood are exhibited for capture by photography or video or digital photography.

With reference to FIGS. 2A and B, a chart is presented showing the intensity of the luminescence of the fluorescein application according to the present invention (refluxed with zinc, hydrogen peroxide solution oxidizing agent, polymer) over time and with first, second and third applications of the solutions to the specimen according to the method of the present invention and in comparison to any background luminescence of the substrate. As can be appreciated from FIGS. 2A and B, the bloodstain-based luminescence is exhibited with greater intensity than of the substrate in all applications and therefor would distinguish the blood stain from the background luminescence of the substrate. Thus the bloodstain, print or the like can easily be photographed.

With reference to FIG. 3, there is shown a comparison between the luminescence of fluorescein according to the present invention. A fluorescin solution in water (NaOH), i.e. prepared according to the water-based reactant discussed in the Background above, is exhibited on the left with the luminescence based upon the present invention exhibited on the right side of FIG. 3. As can be appreciated, the alcohol/acid solubilized and buffered reactant solution according to the present invention produces a more intense luminescence from which greater detail, including ridge detail of a print, can be ascertained.

The reactant solution according to the present invention can be pre-made and has a longer shelf life than water-based fluorescin solutions.

Further, the reactant solution is preferably only slightly basic and therefor is not likely to damage or mar the substrate or injure the technician using the solution.

In a kit, the reactant solution would be provided in a container, such a pump spray bottle containing zinc. The components for mixing the oxidizer would also be provided along with a spray bottle therefor. Alternatively, the oxidizer would be a powder, as described above, supplied in a container for either dusting onto the surface or added o a second spray bottle. At the scene or lab, solvent (ethanol) is added to the spray bottle(s). If the surface tension additive is to be separately applied, i.e. is not included in the buffer and final reactant solution, the additive would also be provided in a separate spray applicator.

Method/Compositions No. 2

For a second embodiment, the reactant Compound A includes dry fluorescein with granular zinc or other reducing agent such as calcium, aluminum, magnesium or other metal. Since the presence of iron will poison the reduction, the reducing agent should be free of iron. Prior to application on the area suspected to have a bloodstain, acetic acid and ethanol are added to Compound A and mixed at room temperature as by shaking such that the reducing agent reduces the fluorescein to fluorescin. Reduction causes the solution to turn from a yellowish color to clear or slightly pinkish in color. If desired, the solution may be buffered to enhance brightness. The, reactant fluorescin solution is nebulized onto the suspected area. The fluorescin of the reactant oxidizes with the blood to produce in those areas where blood is present, fluorescein. Depending upon the characteristics of the surface, as described above, a surface tension additive may by applied to the surface or included in a buffer (if the solution is buffered).

For this embodiment, buffering of the reactant solution of compound A may not be required since careful control of the pH is not necessary.

The oxidizing agent of compound B may be sodium metaborate, monosodium metaborate, sodium borate or the like in a dry, powder, form or in a liquid form of sodium metaborate, monosodium metaborate or sodium borate in ethanol or, more preferably, water or hydrogen peroxide, as described above. Afer application of the reactant fluorescin solution, the compound B is dusted or nebulized over he suspected area.

In response to UV light, e.g. wavelengths of approximately between 400 and 500 nm, the reacted fluorescein fluoresces for photographic detection and capture of the blood-print.

As can be appreciated, this embodiment is well suited to be distributed to law enforcement in a kit. Compound A (dry) in a spray applicator, buffer (if desired), surface tension additive and Compound B (dry) as well as the acetic acid and ethanol for reducing compound A would be provided. The reactant would be made fresh prior to application.

While we have shown certain embodiments of the present invention, it is to be understood that is subject to many modifications without departing from the spirit and scope of the appended claims.

We claim:

1. A method for detecting bloodstains on a surface comprising:
   (a) mixing at substantially room temperature fluorescein or dicholorofluorescein in a solution of acetic acid, ethanol and a reducing agent selected from a group consisting of metals excluding iron, said reducing agent reducing the fluorescein or dicholorofluorescien to a reduced solution of fluorescin or dicholorofluorescin;
   (b) buffering the solution to a pH of approximately between 8 and 10;
   (c) applying the reduced solution to the surface suspected of containing the bloodstain, said reduced solution reacting with the bloodstain to produce fluorescein or dicholorofluorescein; and
   (d) irradiating the area with UV light in wavelengths of approximately between 400 and 500 nm to reveal the bloodstain.

2. The method of claim 1 comprising solubilizing the fluorescein or dicholorofluorescein with said reducing agent selected from the group consisting of zinc, calcium, aluminum and magnesium.

3. The method of claim 1 comprising warming the solution during step (a).

4. The method of claim 1 comprising applying an oxidizer to the surface.

5. The method of claim 4 comprising applying an oxidizer selected from the consisting of hydrogen peroxide, sodium metaborate, monosodium metaborate and sodium borate.

6. The method of claim 1 comprising applying to said surface a surface tension reducing composition.

7. The method of claim 6 comprising applying to said surface a surface tension reducing agent selected from the group consisting of a polymer and a surfactant.

8. The method of claim 1 comprising warming the solution during mixing.

9. A kit for the preparation of compounds for use in, detecting of bloodstains using UV light, said kit comprising:
   (a) dry fluorescein with dry reducing agent selected from a group consisting of zinc, calcium, aluminum and magnesium and excluding iron;
   (b) liquid solvent of ethanol and acetic acid;
   (c) a mixing bottle for mixing the compounds of (a) with the solvent of (b) to reduce fluorescein to fluorescin;
   (d) a buffer to add to the reduced solution to buffer the solution to a pH of approximately between 8 and 10;
   (e) a spray bottle for spraying the reduced and buffered solution of (d) onto a surface suspected of containing a bloodstain; and
   (f) a source of UV light to illuminate the suspected area.

10. The kit of claim 9 comprising a oxidizer to apply to the surface between steps (e),and (f).

11. The kit of claim 9 comprising a surface tension reducing agent.

* * * * *